United States Patent [19]
Davies

[11] Patent Number: 5,258,175
[45] Date of Patent: Nov. 2, 1993

[54] TREATMENT OF POISONING AND COMPOSITIONS FOR USE THEREIN

[75] Inventor: Donald S. Davies, Beaconsfield, United Kingdom

[73] Assignee: M L Laboratories PLC, London, England

[21] Appl. No.: 646,939

[22] Filed: Jan. 25, 1991

[30] Foreign Application Priority Data

Jan. 25, 1990 [GB] United Kingdom ............... 9001687

[51] Int. Cl.⁵ .................. A61F 2/02; A61K 9/14; A61K 31/715; A61K 47/36
[52] U.S. Cl. .................... 424/78.3; 424/422; 424/423; 424/424; 424/425; 424/484; 424/488; 514/54; 514/58; 514/772; 514/772.1; 514/772.3; 514/778; 514/781; 514/823; 536/46; 536/103
[58] Field of Search ............ 424/422, 423, 424, 425, 424/484, 488, 78.3; 514/54, 58, 781, 823, 772, 772.1, 772.3, 778; 536/46, 103

[56] References Cited

U.S. PATENT DOCUMENTS

| | | | |
|---|---|---|---|
| 4,020,160 | 4/1977 | Bernstein et al. | 424/180 |
| 4,066,829 | 1/1978 | Nair et al. | 536/103 |
| 4,247,535 | 1/1981 | Lewis et al. | 536/112 |
| 4,339,433 | 7/1982 | Kartinos et al. | 424/180 |
| 4,886,789 | 12/1989 | Milner | 514/60 |

OTHER PUBLICATIONS

Chemical Abstracts 75, Abstract 121407, 1971 (Abstracting JP 71-25021) Morii et al.
Amaizo—Technical Information—Amaizo Fro--Dex ®.

Primary Examiner—Thurman K. Page
Assistant Examiner—Carlos Azpuru
Attorney, Agent, or Firm—Darby & Darby

[57] ABSTRACT

A dextrin derivative, in which a proportion of the hydroxyl groups in the dextrin have been replaced by strongly acidic groups, is useful in treatment of poisoning or drug overdose, particularly by compounds having basic groups. Dextrin sulphate is a preferred derivative for use in the treatment of paraquat poisoning.

20 Claims, 2 Drawing Sheets

TREATMENT OF POISONING AND COMPOSITIONS FOR USE THEREIN

This invention relates to the treatment of poisoning, and compositions for use in such treatment. The term "poisoning" as used herein is intended to cover not just the inadvertent or deliberate taking of materials which are known poisons but also the deliberate or inadvertent taking of overdose amounts of materials which are not normally regarded as poisons, for example, medicines or drugs.

British patent specification No. 2,154,469A discloses a method of treating a patient for poisoning comprising effecting peritoneal dialysis by introducing into the abdominal cavity of the patient a peritoneal dialysis composition including as an osmotic agent a dextrin consisting of a glucose polymer mixture containing at least 15% by weight of glucose polymers of D.P (degree of polymerisation) greater than 12.

It has now been found that certain poisons can be particularly effectively treated by means of certain dextrin derivatives rather than dextrin itself.

According to the present invention there is provided the use in the treatment of poisoning of a dextrin derivative in which at least a proportion of the hydroxyl groups in dextrin are substituted by strongly acidic groups, for example, sulphate, nitrate or phosphate groups, or mixtures thereof.

The present invention also provides a composition for use in the treatment of poisoning comprising such a dextrin derivative in combination with a pharmaceutically acceptable carrier or diluent.

The present invention also provides a method of treating a human or animal subject suffering from poisoning comprising administering to said subject an effective amount of such a dextrin derivative.

Figure 1:
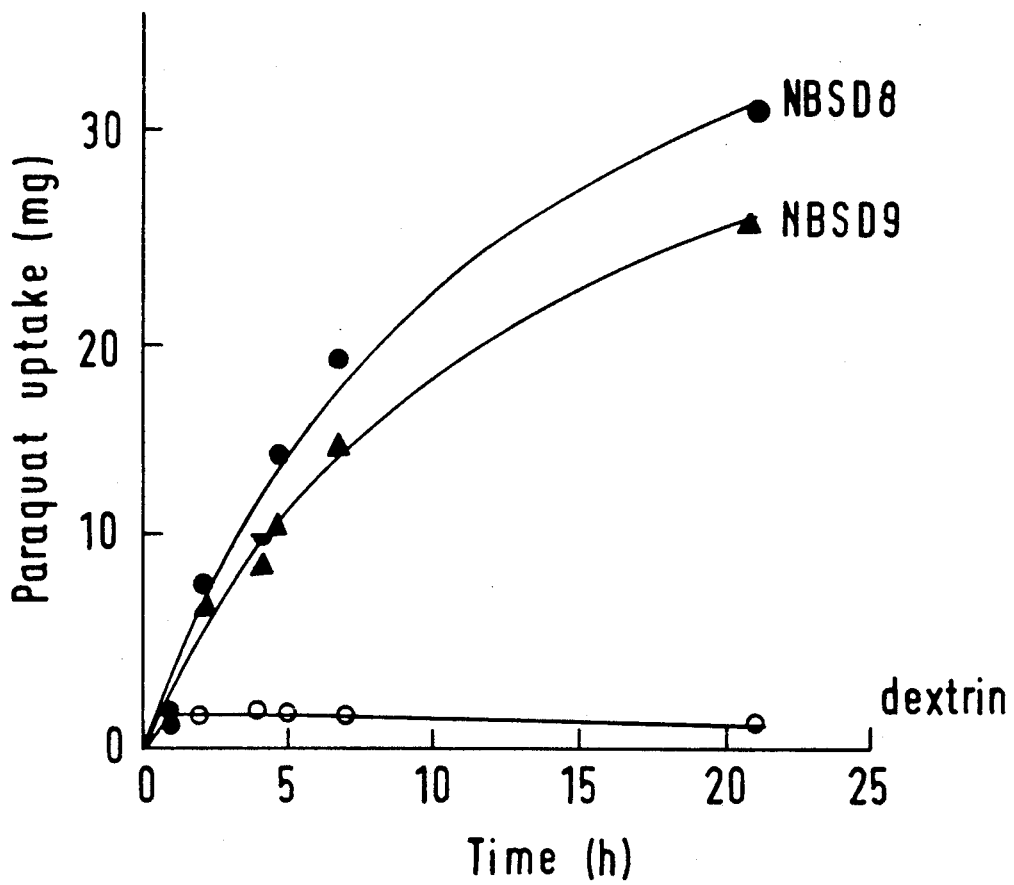
FIG. 1 graphically illustrates the ability of dextrin sulphate derivatives NBSD9 to uptake paraquat over time.

The dextrin derivatives of use in the present invention are particularly effective against poisons in the form of compounds having basic groups. Such a poison is the well known weed-killer paraquat which is the trade name for 1,1-dimethyl-4-4dipyridinium dichloride. Other basic poisons include diquat and ethyleneimine.

In addition to the above mentioned materials which are considered to be poisons as such, the dextrin derivatives of use in the present invention are also particularly effective against materials which are normally used as medicines or pharmaceuticals but which may have damaging effects when taken in overdose. These medicines or pharmaceuticals include those with basic groups of which the following are examples:- amitriptyline, chlorpromazine, dextropropoxyphene, imipramine and trimipramine.

The dextrin derivative can be taken by any appropriate method and the most suitable might well depend on the nature of the poison and the way in which it has been assimilated, for instance, orally or parenterally. Accordingly, in the appropriate cases the dextrin derivative may be administered orally, enterally, parenterally or intraperitoneally.

Where the dextrin derivative is to be administered intraperitoneally, it is preferred that the derivative is derived from a dextrin which is a glucose polymer mixture containing at least 15%, preferably at least 50%, by weight of glucose polymers of D.P (degree of polymerisation) greater than 12.

Preferably, the dextrin has an average molecular weight (a weight average molecular weight) of from 15,000 to 25,000.

A particular dextrin derivative of use in the present invention is a dextrin sulphate with up to 3 sulphate groups per glucose unit. Preferred compositions include those having dextrin sulphate with from 0.5 to 1.5 sulphate groups per glucose unit.

The present invention will now be described with reference primarily to the treatment of paraquat poisoning by means of peritoneal dialysis compositions containing dextrin sulphate. Dextrin sulphates are known compounds (see for example UK Patent 871590 and U.S. Pat. No. 4066829).

It has been found that dextrin sulphate adsorbs paraquat. When dextrin sulphate is incorporated into a peritoneal dialysis solution used to treat paraquat poisoning, the dextrin sulphate serves to reduce the concentration of free paraquat in the dialysate; this has the effect of maintaining a large concentration gradient between the paraquat in the blood and the free paraquat in the dialysate. The efficiency of the dialysate in removing paraquat from the blood is thereby increased.

Preferably, the dialysis solution should provide between 50 and 250 mmoles of sulphate, typically contained within about 2 litres of solution. More preferably, the solution should provide between 100 and 200 mmoles of sulphate, most preferably about 180 mmoles. In theory, each 100 mmoles of sulphate will remove 50 mmoles of paraquat.

Dextrin sulphate may be prepared by first hydrolysing starch to produce dextrin. The product may then be sulphated with any suitable sulphating agents, examples being sulphur trioxide, chlorosulphonic acid and a trimethylamine/sulphur trioxide complex. To limit degradation of the dextrin, these sulphating agents may be used in combination with a Lewis base, such as pyridine.

Dextrin sulphates can be characterised by the sulphate content or sulphur content of the polymer mixture and by the molecular weight distribution of the polymer mixture. The dextrin sulphates used in peritoneal dialysis according to the present invention are selected to be water-soluble since it is important that they do not precipitate from solution in the peritoneum. This is readily achieved in practice; for example the sulphated derivatives of the water-soluble glucose polymer mixtures previously used as osmotic agents in peritoneal dialysis (such as those described in British specification nos. 2,132,914A and 2,154,469A) are water-soluble.

Peritoneal dialysis solutions for normal use in the treatment of end stage renal disease contain electrolytes of a nature and in concentrations comparable with those present in normal human plasma. They also contain an osmotic agent, at present usually dextrose, which serves to create an osmotic pressure gradient across the peritoneal membrane. Under the influence of this pressure gradient, there is a net flow of water and metabolites (such as urea and creatinine) across the peritoneal membrane into the abdominal cavity. When used for treating paraquat poisoning by means of peritoneal dialysis, the compositions of the invention preferably include electrolytes similar to those contained in the conventional solutions used in peritoneal dialysis. For example, they may include electrolytes in the following concentrations (all in mmol/l)

| | |
|---|---|
| Na | 115 to 140 |
| Cl | 95 to 145 |
| Mg | 0.6 to 0.9 |
| Ca | 1.0 to 5.0 |
| Lactate | 30 to 40 |

It is important that the compositions of the invention contain an osmotic agent in a concentration capable of producing efficient and sustained ultrafiltration (a term used to mean the net flow of fluid across the membrane into the peritoneal cavity). The osmotic agent in the compositions of the invention is normally the dextrin sulphate itself, although it can be supplemented, when appropriate, by the inclusion of other osmotic agents, for example dextrose or a mixture of glucose polymers. When a mixture of glucose polymers is used, this can be a mixture of oligosaccharides (polymers with a D.P. of from 2 to 10) or a mixture, such as those disclosed in British patent specifications Nos. 2,132,914A and 2,154,469A, which contain at least 15%, preferably more than 50%, of polymers of D.P. greater than 12.

In one specific method of preparation of a dextrin sulphate, 100 ml of chlorosulphonic acid was added slowly to 400 ml of pyridine, under cooling by means of a mixture of acetone and solid carbon dioxide. The resulting solution was heated to 60° C. and 50 g of a dextrin was added. This dextrin was a mixture of glucose polymers prepared as described in example 2 of the British patent specification No. 2,154,469A. It contained 91.9% of polymers of D.P greater than 12 and 7.9% of polymers of from D.P. 2 to 10, and had an average molecular weight, as determined by H.P.L.C., of 23,700.

After maintaining the reaction mixture at 70° C. for four hours, the mixture was cooled. It was then diluted with 3.0 litres of water, and 10.0 litres of ethanol was added to precipitate the sulphated product.

The product was purified by re-dissolving it in 1.5 litres of water, neutralising with sodium hydroxide solution, and reprecipitating it by addition of 4.0 litres of ethanol. The product was re-dissolved in 1.8 litres of water, transferred to "Viskene" cellophane tubing, and dialysed against water for 48 hours. The pH of the solution of the product was adjusted to 7.5 and the solution was evaporated under vacuum to a volume of 500 ml. The solid product was then isolated by freeze drying. The sulphur content of the product was 0.4 sulphate groups per glucose unit (D/S).

In an alternative and preferred procedure for preparing a dextrin sulphate, dextrin was reacted with trimethylamine/sulphur trioxide complex and sodium carbonate in water at about 65° C. for one hour. The product was isolated by dialysis. The i.r spectra in KBr disc of the product showed absorbence at 1240 and 820 cm$_1$ attributable to sulphate. The intensity of absorption increases with increasing amount of sulphating agent.

Sulphation of dextrin with trimethylamine/sulphur trioxide can product being isolated by dialysis after adding sodium carbonate and the sulphur content being roughly comparable to that obtained in water.

The following Examples 1-7 illustrate methods for the preparation of dextrin sulphate. In each of these Examples the starch dextrin was the aforementioned dextrin of Example 2 of British patent specification No. 2,154,469A.

EXAMPLE 1

A solution of 1 g of starch dextrin in 10 mL of water was stirred at 65–70C. A mixture of 0.5 g of sodium carbonate decahydrate and 0.5 g of trimethylamine-sulphur trioxide complex was added in three portions over 30 minutes with continual stirring. After a further 30 minutes the solution was dialysed against running tap water for three days and then against distilled water for one day. The resultant solution was freeze dried to give 0.55 g of a colourless solid containing 2.9% of sulphur.

EXAMPLE 2

Example 1 was repeated with 1 g of starch dextrin but using 1 g of sodium carbonate decahydrate and 1 g of trimethylamine sulphur trioxide complex to give 0.5 g of product containing 4.1% of sulphur.

EXAMPLE 3

Example 1 was repeated with 1 g of dextrin but using 2 g of sodium carbonate decahydrate and 2 g trimethylamine sulphur trioxide complex to give 0.6 g of colourless product containing 5.3% of sulphur.

EXAMPLE 4

A solution of 20 g of starch dextrin in 70 mL of distilled water was stirred at 65–70° C. and 60 g of sodium carbonate decahydrate and 60 g of trimethylamine sulphur trioxide complex were added in three portions over one hour. The stirring was continued at 70° C. for 5 hours. The brown mixture was filtered, and the solid washed with three 25 mL portions of water then dried to give 26 g of unreacted triethylamine sulphur trioxide complex. The solution was dialysed for three days against running tap water and for one day against distilled water and then freeze dried to give 22 g of product.

EXAMPLE 5

A solution of 20 g starch dextrin in 75 mL of distilled water was stirred at 70° C. and 30 g of trimethylamine sulphur trioxide complex and 8.5 g of sodium hydroxide in 20 mL of water were added in portions over one hour resulting in evolution of triethylamine gas. Three g of charcoal was added to the brown solution, which was filtered through Celite and dialysed against running tap water for 3 days and then against distilled water for 1 day. The resultant solution was freeze dried to give 18.8 g of product containing 12% of sulphur.

EXAMPLE 6

A solution of 40 g of starch dextrin in 100 mL of distilled water was stirred at ambient temperature and 60 g of trimethylamine/sulphur trioxide complex and 16.8 g of sodium hydroxide in 40 mL of water were added in portions over six hours. After a further six hours a solution of 11 g of sodium hydroxide in 20 mL of water was added. The solution was dialysed for three days against running tap water and for one day against distilled water and then freeze dried to give 66 g of product.

EXAMPLE 7

A solution of 10 g of starch dextrin in 100 mL of dry N,N-dimethylformamide was stirred at 70° C. and 10 g of cyclamic acid added. After four hours a solution of 33 g of sodium acetate in 75 mL of water was added to give thick slurry, which was added with stirring to 750 mL of ethanol. The mixture was stored at 4° C. overnight then centrifuged at 18,000 rpm for 1 hour. The solid was resuspended in ethanol and recentrifuged. The solid material was dried in vacuo over phosphorus pentoxide then dissolved in 220 mL of water containing 50 g of sodium acetate and dialysed for three days against tap water and for one day against distilled water. The resultant solution was freeze dried to give colourless solid product.

The following Examples 8–11 illustrate the use of dextrin sulphate in the treatment of paraquat poisoning in which the dextrin derivative contains from 0.4 to 1.02 sulphate groups per glucose unit.

EXAMPLE 8

Five ml of a 2% solution of two dextrin sulphates and an unsubstituted dextrin in 0.01M phosphate buffer, pH 7.4, were placed in dialysis bags (made by knotting an appropriate length of Viskene dialysis tube). The dialysis membrane is permeable to small molecules including paraquat but the dextrin and dextrin sulphate cannot cross the membrane. The bags containing the solutions were placed in beakers containing 200 ml of 0.01 M phosphate buffer, pH 7.4, containing 100 mg of carbon-14 labelled paraquat. The solutions in the beakers were stirred and the rate of accumulation of paraquat within the dialysis bag was measured over 21 hours. The results given in accompanying FIG. 1 show that a dialysis bag containing the unsubstituted dextrin merely equilibrates with the solution outside the bag in terms of paraquat concentration (Table 1) but bags containing a dextrin sulphate (NBSD9) with 0.4 sulphate groups per glucose unit or a dextrin sulphate (NBSD8) with 1.02 sulphate groups per glucose unit accumulate paraquat against a concentration gradient to concentrations which are 12 and 17 times those in the dialysis solution (Table 1). These results demonstrate that paraquat crosses the semi-permeable membrane of the dialysis bag and is adsorbed by dextrin sulphate but not dextrin held within the dialysis bag. The unsubstituted dextrin was the aforementioned dextrin prepared as described in Example 2 of British Patent Specification No. 2,154,469A. The dextrin sulphates designated NBSD9 and NBSD8 were produced by sulphation of this dextrin.

TABLE 1

Paraquat concentrations within and outside the dialysis bag at 0 and 21 hours

| | Paraquat (mg/ml) | | | | |
| --- | --- | --- | --- | --- | --- |
| | Time 0 | | Time 21 hours | | |
| Polymer in bag | Bag | Solution | Bag | Solution | Ratio+ |
| Dextrin | 0 | 0.5 | 0.4 | 0.5 | 0.8 |
| Dextrin Sulphate | | | | | |
| NBSD9 (D/S 0.40) | 0 | 0.5 | 5 | 0.4 | 12.5 |
| NBSD8 (D/S 1.02) | 0 | 0.5 | 6 | 0.35 | 17.1 |

+Ratio Concentration in bag/Concentration outside

EXAMPLE 9

Figure 2:
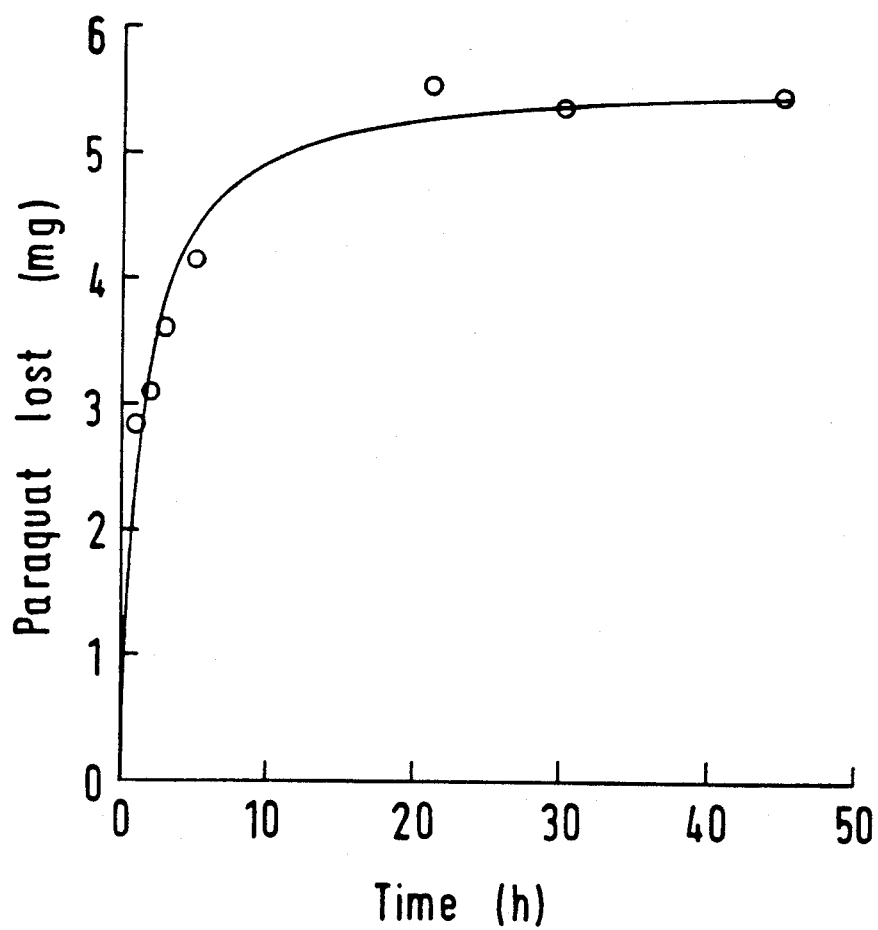
FIG. 2 graphically illustrates the loss of paraquat from a dextrin sulphate solution over time.

In a variation of Example 8, 100 mg of paraquat was added to 1 ml of a 50% solution of dextrin sulphate in a dialysis bag and dialysed against 100 ml of the buffer used in Example 1. This experiment was conducted to demonstrate that dextrin sulphate would hold paraquat within the bag against a concentration gradient. The result in FIG. 2 shows that only 5% of the paraquat was lost from the bag over a period of 50 hours. Thus 95 mg was retained. If we assume a volume for the total system of 100 ml then the free concentration of paraquat in solution is 0.05 mg/ml or only 0.05% of the total within the bag.

EXAMPLE 10

This Example demonstrates that a solution of dextrin sulphate placed in the peritoneal cavity adsorbs paraquat from the blood stream in rats. The rat is not the ideal surrogate for man since, unlike in man, glucose polymer placed in solution in the peritoneal cavity is rapidly taken up into the blood stream. However, the studies in rats demonstrated that dextrin sulphate in the peritoneal cavity did accumulate paraquat from the blood stream against a concentration gradient.

Carbon-14 labelled paraquat (20 ml/kg PQ ion) was administered to rats in an oily vehicle by subcutaneous injection. Paraquat is released slowly from the site of injection to give a steady blood plasma concentration over the course of the experiment. Two hours after administration of the paraquat, 10 ml of a 2% solution of an unsubstituted dextrin or a dextrin sulphate with 1.0 sulphate groups per glucose unit (NBSD22) was injected into the peritoneal cavity. At 3 hours samples of blood, plasma and peritoneal fluid were obtained and analysed for radioactive paraquat. The experiment was conducted on two occasions with 3 animals per treatment group. The results, summarised in Table 2, demonstrate that paraquat accumulated in the peritoneal cavity against a concentration gradient if dextrin sulphate was present but not with dextrin. Peritoneal fluid/blood plasma ratios for dextrin sulphate were twice those of dextrin. This is despite the fact that the rat is a poor model because of rapid loss (50 to 60% in 1 hour) of sugar polymer from the peritoneal cavity. The unsubstituted dextrin was the same as that of Example 8 and the dextrin sulphate designated NBSD22 was produced by sulphation of this dextrin.

TABLE 2

| | Dialysate fluid/blood plasma ratios for paraquat+ | |
| --- | --- | --- |
| Dialysate | Experiment 1 (n-3) | Experiment 2 (n-3) |
| 2% Dextrin | 0.51 | 0.72 |
| 2% Dextrin sulphate | 1.12 | 1.39 |

+1 hour after insertion of dialysate fluid into peritoneal cavity.

EXAMPLE 11

The aforementioned dextrin of Example 2 of British Patent Specification No. 2,154,469A was used to make up a solution of the type conventionally used in peritoneal dialysis. The solution contained 5% of the dextrin and, in addition, 2.5% of that dextrin sulphate designated NBSD8 in Example 8 and containing 1.02 sulphate groups per glucose unit. Two litres of such a solution, fed into the peritoneum, are capable of adsorbing more than 3.5g of paraquat. The solution may conveniently be changed every 6 hours.

The amount of dextrin sulphate may be varied either to increase the total number of sulphate groups or, in the case where the dextrin sulphate has more sulphate groups per glucose unit, in order to keep the total number of sulphate groups at about the same level. It is preferred, however, that the total dextrin concentration (dextrin plus dextrin sulphate) be about 7½% in order to achieve an appropriate dialysis rate and, accordingly, the amount of dextrin is preferably increased if the dextrin sulphate content is altered.

As has been mentioned above, the use of dextrin sulphate for the treatment of paraquat poisoning is not confined to peritoneal dialysis. One existing method of treating paraquat poisoning is haemodialysis; the efficiency of this treatment can be improved by including dextrin sulphate in the dialysis solution. Another treatment involves oral administration of an adsorbent for paraquat, usually Fuller's Earth. The constipatory action of the latter adsorbent is disadvantageous; there is a clear advantage in replacing it partly or entirely by oral administration of an aqueous solution of dextrin sulphate.

I claim:

1. A method of treating a human or animal subject suffering from poisoning, comprising enterally or parenterally administering to said subject an effective amount of a dextrin derivative for the binding of the poison wherein the dextrin is substituted at its hydroxyl groups with up to three strongly acidic groups per glucose unit, wherein the dextrin derivative is derived from a dextrin which is a glucose polymer mixture comprising at least 15% by weight of glucose polymers of D.P. greater than 12 and having an average molecular weight of 15,000 to 25,000.

2. The method of claim 1, wherein said acidic groups are selected from the group consisting of sulphate groups, nitrate groups, phosphate groups and mixtures thereof.

3. The method of claim 1, wherein the acidic groups are sulphate groups.

4. The method of claim 1, wherein the dextrin derivative has from 0.5 to 1.5 sulphate groups per glucose unit.

5. The method of claim 1, wherein the glucose polymer mixture contains at least 50% by weight of glucose polymers of D.P. greater than 12.

6. The method of claim 1, wherein the dextrin derivative is orally administered.

7. The method of claim 1, wherein an aqueous solution of the dextrin derivative is intraperitoneally administered.

8. The method of claim 1, wherein the subject is suffering from poisoning by a compound having basic groups.

9. The method of claim 8, wherein the subject is suffering from paraquat poisoning.

10. The method of treating a human or animal subject suffering from poisoning, comprising heamodialyzing said subject with a dialysis solution containing a dextrin derivative which is substituted at its hydroxyl groups with up to three strongly acidic groups per glucose unit.

11. The method of claim 10, wherein said acidic groups are selected from the group consisting of sulphate groups, nitrate groups, phosphate groups and mixtures thereof.

12. A pharmaceutical composition for use in the treatment of poisoning, the composition comprising a dextrin derivative which is substituted at its hydroxyl groups with up to three strongly acidic groups per glucose unit wherein the dextrin derivative is derived from a dextrin which is a glucose polymer mixture comprising at least 15% glucose polymers of D.P. greater than 12 and having an average molecular weight of 15,000 to 25,000 and a pharmaceutical carrier or diluent therefor.

13. The pharmaceutical composition of claim 12, wherein said dextrin derivative has 0.5 to 1.5 sulfate groups per glucose unit.

14. The pharmaceutical composition of claim 12, which comprises an aqueous solution suitable for use in peritoneal dialysis.

15. The pharmaceutical composition of claim 12, wherein said glucose polymer mixture comprises at least 50% glucose polymers of D.P. greater than 12.

16. A dextrin derivative which is substituted at its hydroxyl groups with up to three strongly acidic groups per glucose unit, wherein the dextrin derivative is derived from a dextrin which is a glucose polymer mixture comprising at least 15% glucose polymers of D.P. greater than 12 and having an average molecular weight of 15,000 to 25,000.

17. The dextrin derivative of claim 16 wherein said dextrin derivative has 0.5 to 1.5 sulfate groups per glucose unit.

18. The dextrin derivative of claim 16, wherein said glucose polymer mixture comprises at least 50% glucose polymers of D.P. greater than 12.

19. The pharmaceutical composition of claim 12, wherein the strongly acidic groups are selected from the group consisting of sulfate groups, nitrate groups, phosphate groups and mixtures thereof.

20. The dextrin derivative of claim 16, wherein said acidic groups are selected from the group consisting of sulphate groups, nitrate groups, phosphate groups and mixtures thereof.

* * * * *